(12) United States Patent
Peters et al.

(10) Patent No.: US 7,615,026 B1
(45) Date of Patent: Nov. 10, 2009

(54) ANKLE BRACE

(75) Inventors: Rick Peters, Indianapolis, IN (US); Randolph Smith, Indianapolis, IN (US)

(73) Assignee: Ultra Athlete LLC, Indianapolis, IN (US)

( * ) Notice: Subject to any disclaimer, the term of this patent is extended or adjusted under 35 U.S.C. 154(b) by 0 days.

(21) Appl. No.: 11/875,448

(22) Filed: Oct. 19, 2007

Related U.S. Application Data

(63) Continuation-in-part of application No. 11/535,829, filed on Sep. 27, 2006.

(51) Int. Cl.
*A61F 5/00* (2006.01)

(52) U.S. Cl. .............................. 602/23; 602/27; 128/882

(58) Field of Classification Search ...................... 602/5, 602/16, 23, 27; 128/882
See application file for complete search history.

(56) References Cited

U.S. PATENT DOCUMENTS

| | | | |
|---|---|---|---|
| 4,517,968 A | 5/1985 | Greene et al. | |
| 4,834,078 A | 5/1989 | Biedermann | |
| 4,865,023 A | 9/1989 | Craythorne et al. | |
| RE33,395 E | 10/1990 | Peters | |
| 4,962,760 A * | 10/1990 | Jones | 602/27 |
| 5,069,202 A | 12/1991 | Prock | |
| 5,445,603 A | 8/1995 | Wilkerson | |
| 5,496,263 A * | 3/1996 | Fuller et al. | 602/27 |
| 5,797,865 A | 8/1998 | McDavid, III | |
| 5,827,210 A * | 10/1998 | Antar et al. | 602/23 |
| 5,944,678 A | 8/1999 | Hubbard | |
| 6,056,712 A * | 5/2000 | Grim | 602/27 |
| 6,186,966 B1 | 2/2001 | Grim et al. | |
| 6,602,215 B1 | 8/2003 | Richie, Jr. | |
| 6,689,081 B2 | 2/2004 | Bowman | |
| 6,767,332 B1 | 7/2004 | Pardue et al. | |
| 6,929,617 B2 | 8/2005 | McCormick et al. | |
| 7,018,352 B2 | 3/2006 | Pressman et al. | |
| 2004/0019307 A1* | 1/2004 | Grim et al. | 602/27 |

* cited by examiner

*Primary Examiner*—Michael A. Brown
(74) *Attorney, Agent, or Firm*—Camoriano and Associates; Theresa Fritz Camoriano

(57) ABSTRACT

An ankle brace provides a variety of features that contribute to comfort, stability, and support. One embodiment provides thin, elongated gripping surfaces on the bottom of the brace, to reduce the opportunity for the brace to slip relative to the wearer's shoe. One embodiment provides substantially horizontal strap-receiving slots in the forefoot area, which; pull the foot down, toward the bottom of the brace, not relying on the shoe to hold the foot down against the brace.

10 Claims, 17 Drawing Sheets

ANKLE BRACE

BACKGROUND

This application is a continuation-in-part of U.S. patent application Ser. No. 11/535,829, filed Sep. 27, 2006.

DETAILED DESCRIPTION

Figure 1:
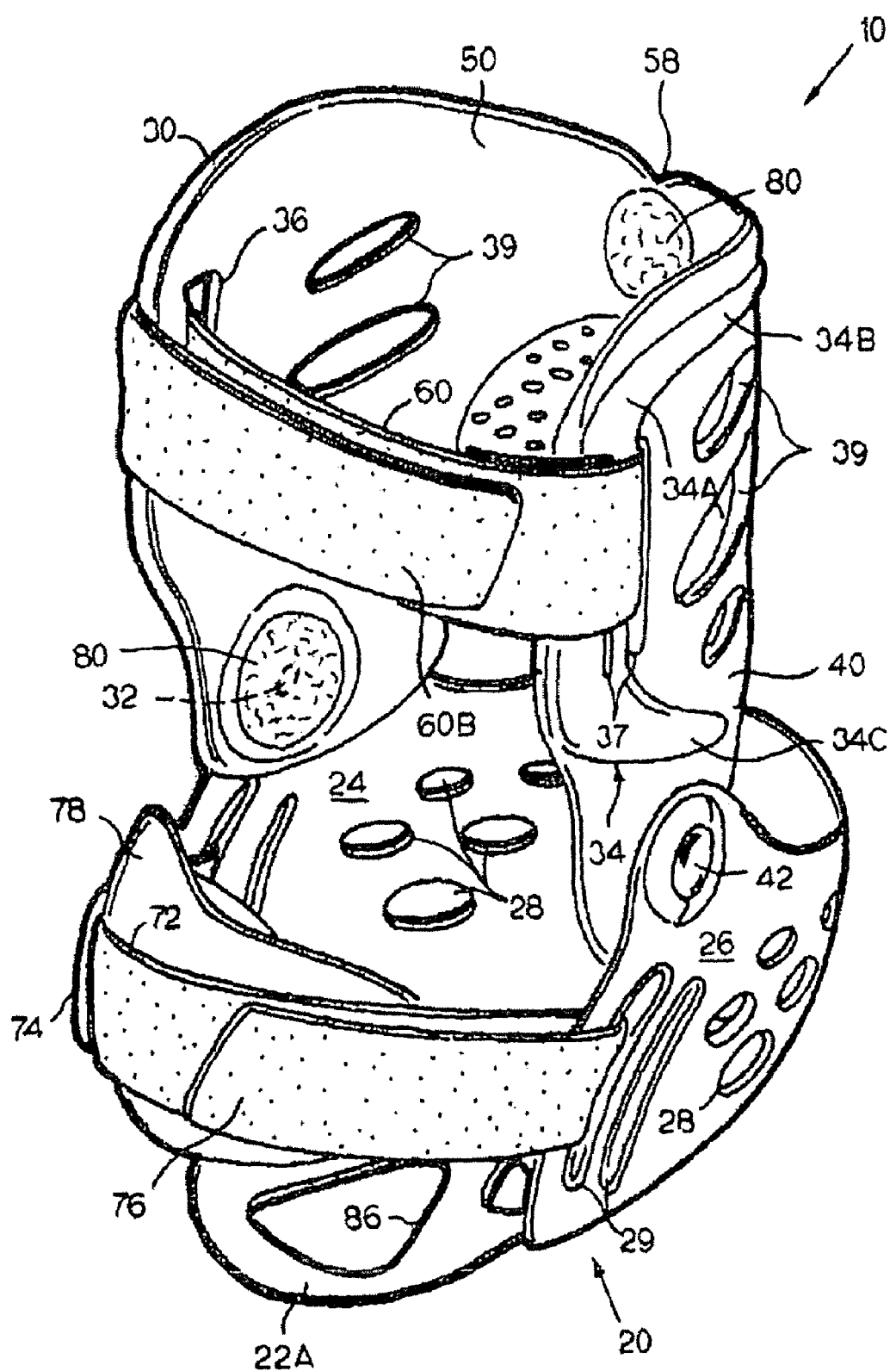
FIG. 1 is a front perspective view of one embodiment of an ankle brace.

FIGS. 1-8 show one embodiment of an ankle brace 10. The basic components of the ankle brace are a substantially U-shaped stirrup 20, a left pivot leg 30, and a right pivot leg 40. The stirrup 20 includes a bottom portion 22, a left upright portion 24, and a right upright portion 26. When worn, the bottom portion 22 extends under the wearer's foot, and the left and right upright portions 24, 26 extend upwardly along the sides of the wearer's foot. A forward projection 22A on the bottom portion 22 is substantially thinner and more flexible than the rest of the stirrup 20, providing for the wearer's comfort. The left and right pivot legs 30, 40 are pivotally attached to the left and right upright portions 24, 26 at left and right pivot points 32, 42, respectively, and are connected together by a rear cuff 50, which extends around the rear of the wearer's leg. The left and right sides of the brace 10 are mirror images of each other, except that the right pivot leg 40 has two vertical slots 37 for receiving an upper adjustment strap 60, while the left pivot leg 30 has only one vertical slot 36 for receiving the upper adjustment strap 60.

This particular ankle brace 10 is made of a polyester-based thermoplastic polyurethane (TPU) resin made by Bayer MaterialScience LLC and sold under the name Texin® 255. This material has a flexural modulus of 20,000 psi at 73 degrees Fahrenheit (a.k.a. room temperature) and a tensile strength of 7,000 psi. A known standard test that is used to determine the flexural modulus of a given material is ASTM D 790, and a standard test for determining the tensile strength is ASTM D412. The flexural modulus for the materials such as polypropylene and nylon that are typically used for prior art rigid braces is well over 100,000 psi. For example, a flexural modulus for polypropylene is typically over 110,000 psi, and may be as high as 600,000 psi. A flexural modulus for nylon is typically over 130,000 psi, and may be as high as 1,200,000 psi. Because this brace 10 is more flexible than prior art rigid braces, it is able to conform more closely to the shape of the wearer's foot. This means that, in many cases, in addition to being more comfortable, it actually can provide better support than a more rigid brace. Prior art wraps such as "Ace" bandages, also are able to conform to the shape of the wearer's foot, but they are too flexible to provide good support. For comfort and support, it is preferable to use a material having a flexural modulus at room temperature (73° F.) between 10,000 psi and 80,000 psi, and more preferable between 10,000 psi and 50,000 psi. It is also desirable for the material to have a tensile strength greater than 4,000 psi in order to maintain structural integrity.

It would be possible to make portions of the brace 10 from different materials, if desired. For example, it would be possible to make the right and left pivot legs 30, 40 from polyurethane and to make the stirrup portion 20 of the brace from traditional, more rigid materials, or the reverse. Of course, other materials besides polyurethane could be used to provide the desired flexural modulus and tensile strength.

Figure 2:
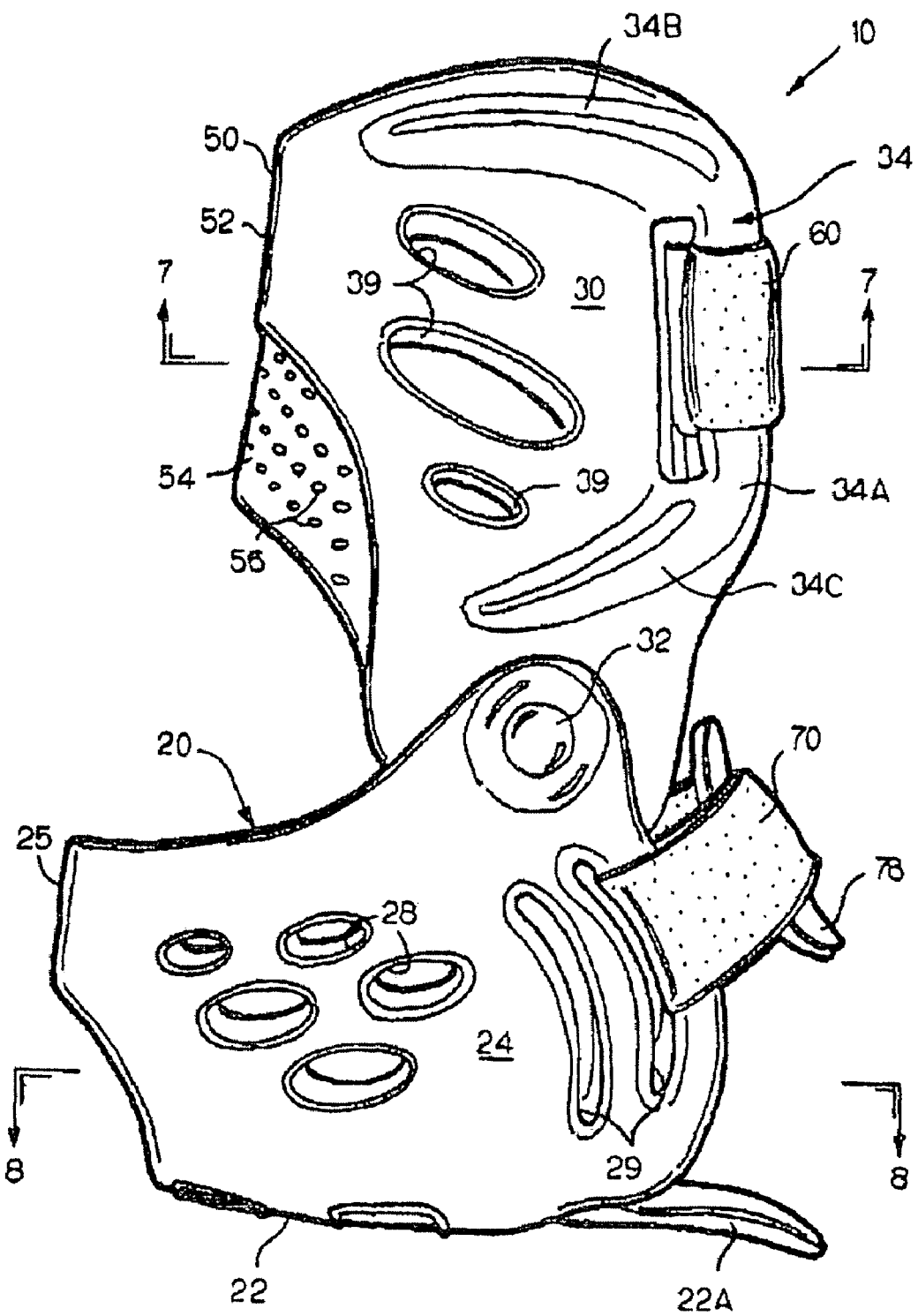
FIG. 2 is a left side view of the ankle brace of FIG. 1.
Figure 7:
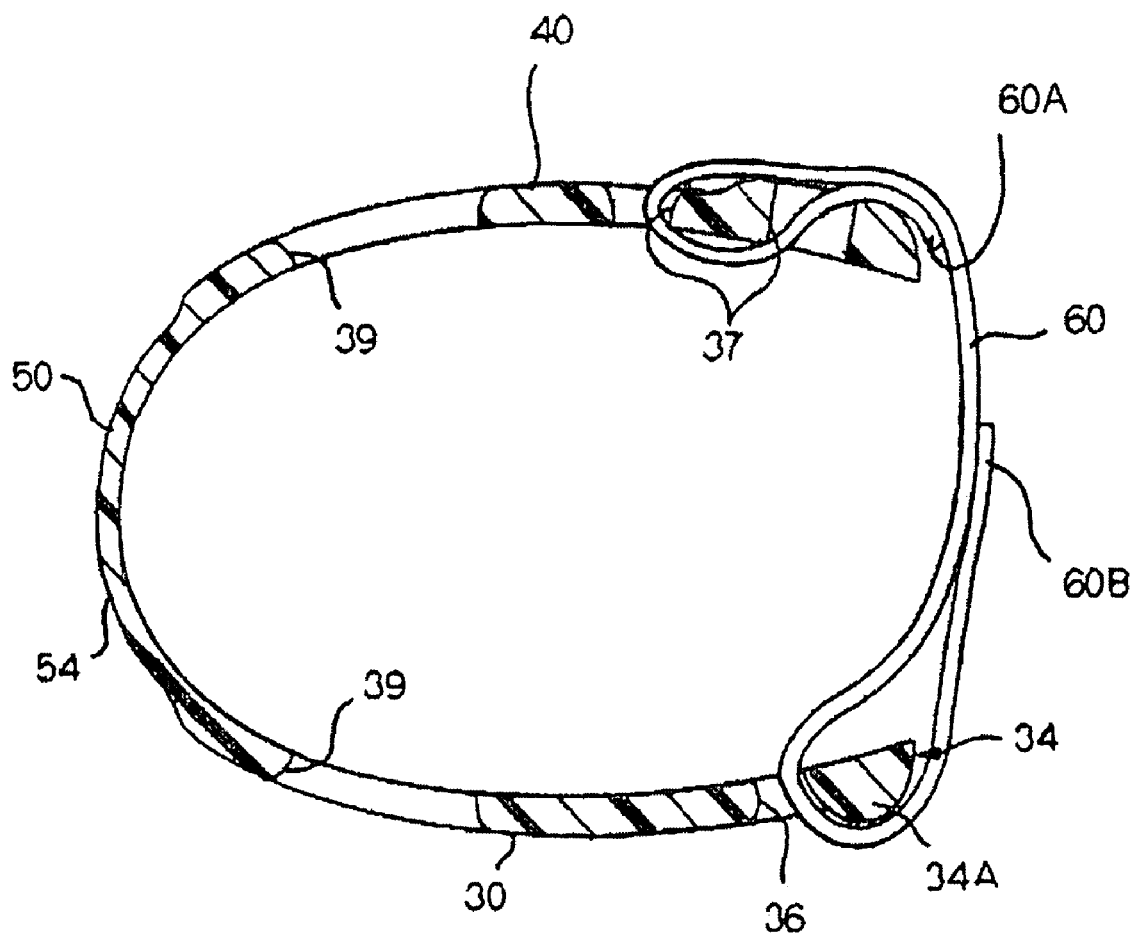
FIG. 7 is a view taken along line 7-7 of FIG. 2.

As best shown in FIGS. 2 and 7, the major portion of the left pivot leg 30 is relatively thin, and there is a raised, U-shaped rib 34 near the front of the leg 30. The right pivot leg 40 is almost a mirror image of the left pivot leg 30, with the only difference being that it has two vertical slots 37, with the front slot being cut through the rib 34A. The U-shaped rib 34 includes a first portion 34A, that extends generally in a top to bottom direction along the front of the pivot leg 30, and second and third portions 34B, 34C that extend generally rearwardly from the top and bottom of the first portion 34A. The major portion of the pivot leg 30 preferably is between 0.050 and 0.150 inches thick, and the U-shaped rib 34 is tapered, being thinner where it blends into the rest of the leg 30 and thicker in the middle. The thickest portion of the rib 34 preferably is, between 0.150 inches and 0.250 inches thick. FIG. 7 best shows that the first portion 34A of the rib 34 is thicker than the major portion of the pivot leg 30.

Referring again to FIGS. 2 and 7, the left pivot leg 30 defines a vertical slot 36 rearwardly and general parallel to the first portion 34A of the rib 34. The slot 36 extends between the second portion 34B and third portion 34C of the rib. The slot 36 receives the upper adjustment strap 60, which includes hook and loop fastener material, such as Velcro®, which is used to tighten the pivot legs 30, 40 against a wearer's leg when in use. As best shown in FIG. 7, the right end 60A of the strap 60 is fed through the two slots 37 in the right pivot leg 40, and then the strap 60 extends across the front of the brace between the two pivot legs 40, 30, through the vertical slot 36, and then wraps back around the front of the brace onto itself. Friction prevents the right end 60A of the strap from coming loose from the right pivot leg 40, and the hook and loop fastener secures the other end 60B of the strap 60 in place. The main function of the rib 34 is to beef up the slot portion of the brace in order to withstand the forces from the strap 60.

Figure 4:
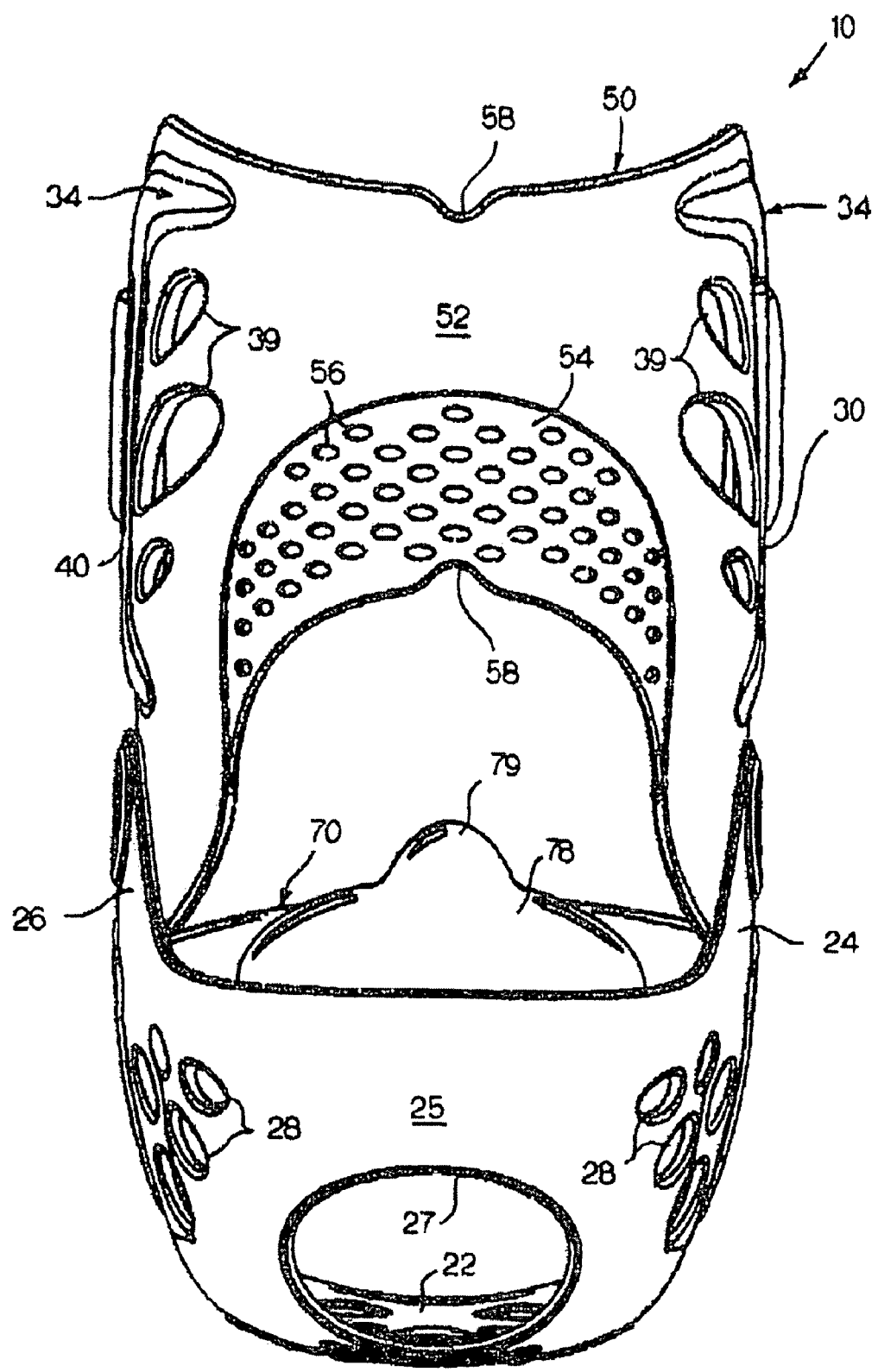
FIG. 4 is a rear view of the ankle brace of FIG. 1.

The right and left pivot legs 30, 40 are connected together in a unitary piece by a cuff 50, which extends around the rear side of the ankle brace 10. (Alternatively, it would be possible to provide a cuff that extends around the front side of the brace or to eliminate the cuff completely.) As best shown in FIG. 4, the cuff 50 includes upper and lower bands 52, 54 having different thicknesses. The lower band 54 is thinner than the upper band 52, with the upper band having a thickness in the same range as the right and left pivot legs 30, 40, and the lower band 54 preferably being between 0.030 inches and 0.050 inches thick. The lower band 54 forms the bottom edge of the cuff 50. This allows the lower portion of the cuff 50 and the bottom edge which impinges on the wearer's leg when he is walking, to be more flexible and the upper portion to provide more support, which helps make the brace 10 more comfortable for the wearer. Of course, the entire cuff 50 could be made of a single thickness, or the thickness of the cuff could vary throughout the cuff, if desired.

The lower band 54 also defines a plurality of openings 56, which are slightly elongated in the left to right direction. The cuff 50 also has vertical indentations 58 at the center top and bottom edges, which reduce the height of the cuff at its center, making it easier for the cuff 50 to flex about a vertical axis at its center.

As best shown in FIG. 2, the right pivot leg 30 defines larger elongated openings 39, which extend in a generally front to back direction, with the front of each opening 39 being a bit lower than the rear. The number, size, and arrangement of the openings 39 may be selected by the designer as desired.

As best shown in FIG. 2, the right upright portion 24 of the stirrup 20 also includes elongated openings 28 which are generally elongated in the front to back direction.

Figure 3:
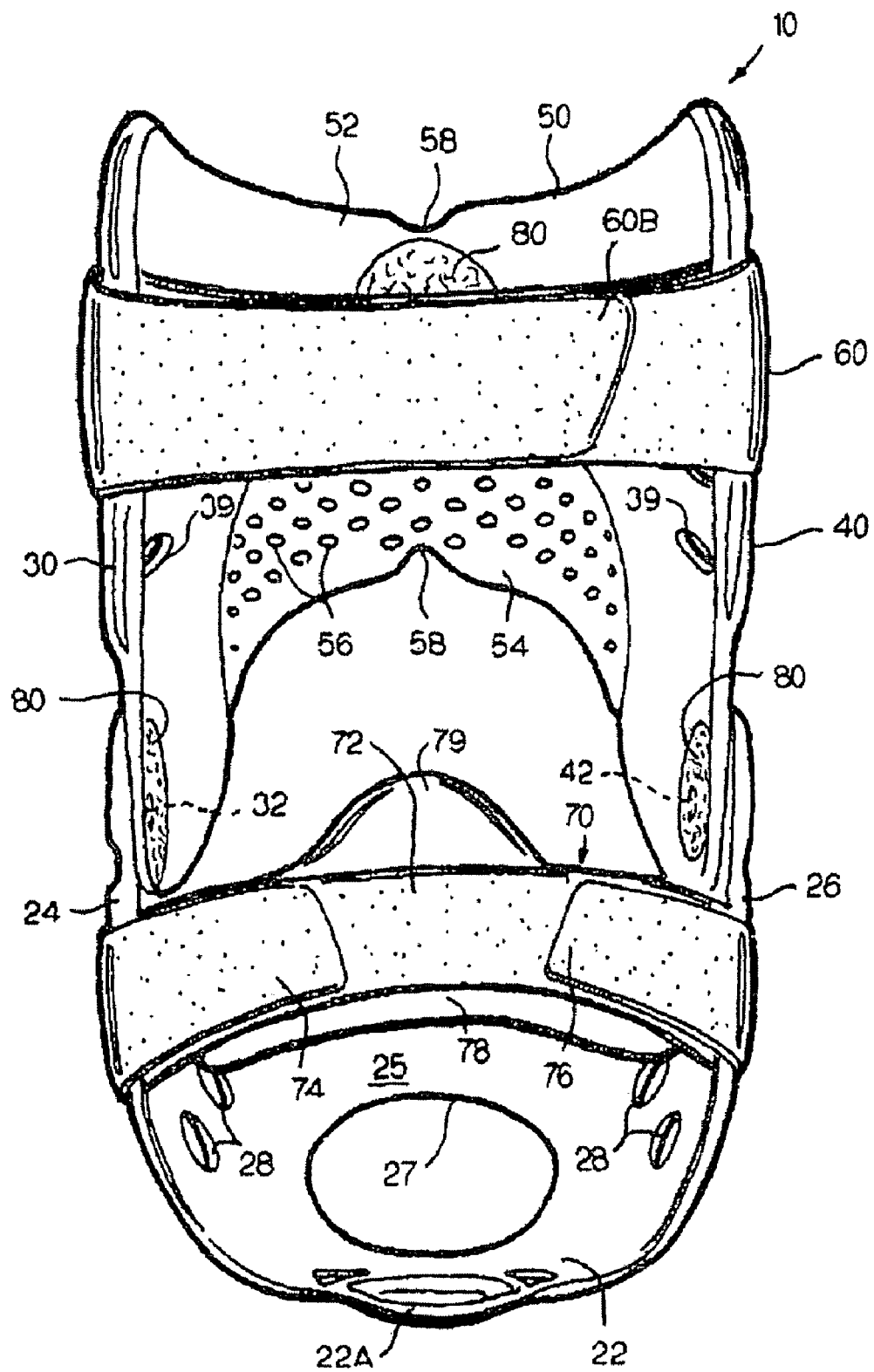
FIG. 3 is a front view of the ankle brace of FIG. 1.
Figure 5:
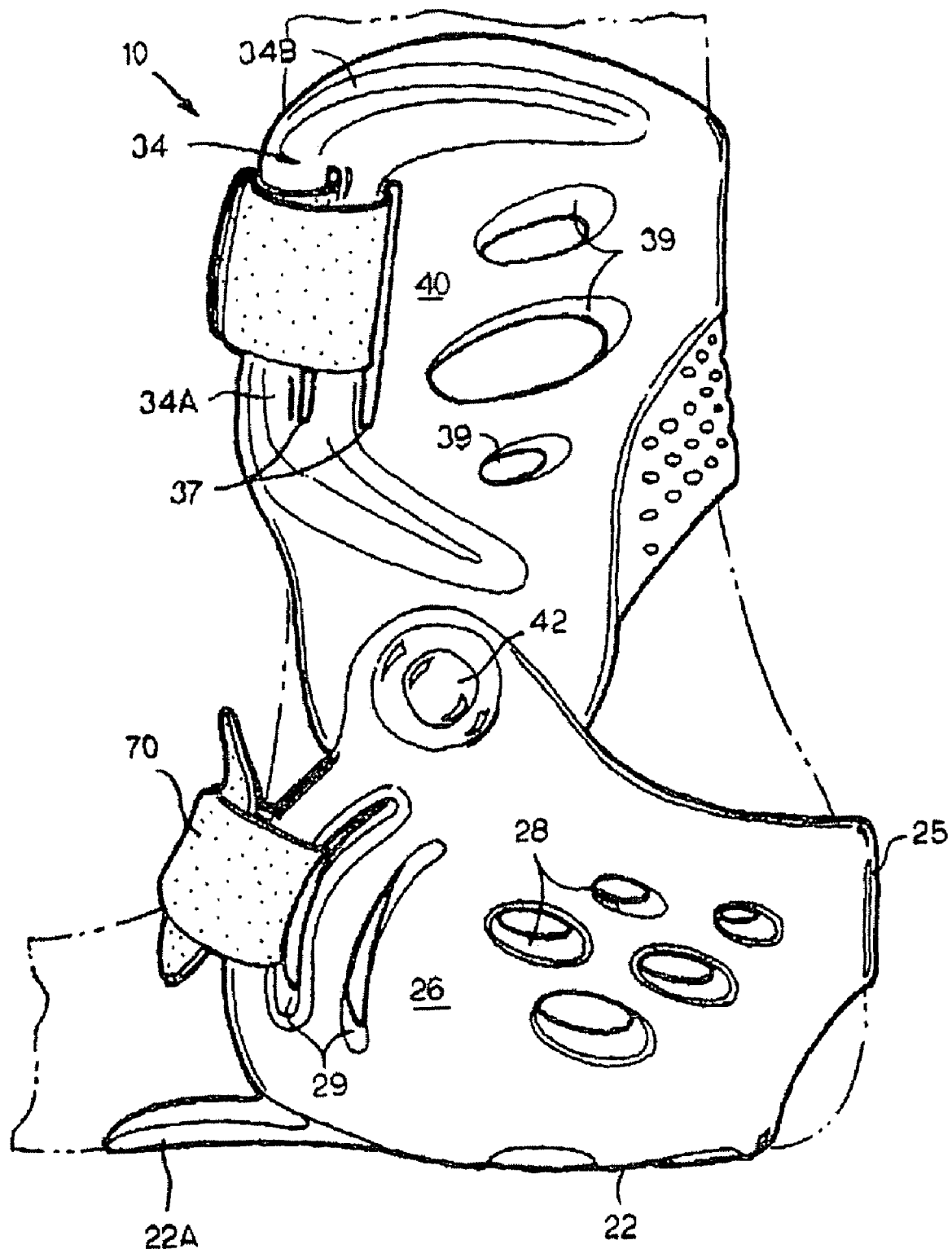
FIG. 5 is a right side view of the brace of FIG. 1 being worn on a human foot.

As best shown in FIGS. 3 and 4, the left and right upright portions 24, 26 are connected at the rear by a heel strip 25. The heel strip 25 and left and right upright portions 24, 26 define a rounded heel opening 27, which receives the wearer's heel, as shown in FIG. 5.

The left and right upright portions 26, 24 also define arcuate strap-receiving slots 29 near their front edge. Each strap-receiving slot 29 is elongated, having first and second ends and first and second sides. The first and second sides extend substantially parallel to the front edge of the respective upright portion, with the first side of each slot 29 lying closer to the front edge of the upright portion than the second side of that slot. In this case, two parallel slots 29 are defined by the left upright portion 26, and two parallel slots are formed by the right upright portion 24. The two parallel slots 29 on each upright portion 24, 26 are aligned side-to-side with each other, with the first side of the second slot 29 adjacent to the second side of the first slot 29. The slots are essentially the same length, and the respective first and second ends of each pair of parallel slots also lie adjacent to each other, so the slots 29 are coextensive with each other for essentially their entire length. These slots 29 receive a lower adjustment strap 70, which is used to tighten the left and right upright portions 24, 26 of the stirrup 20 to the wearer's foot.

Figure 6:
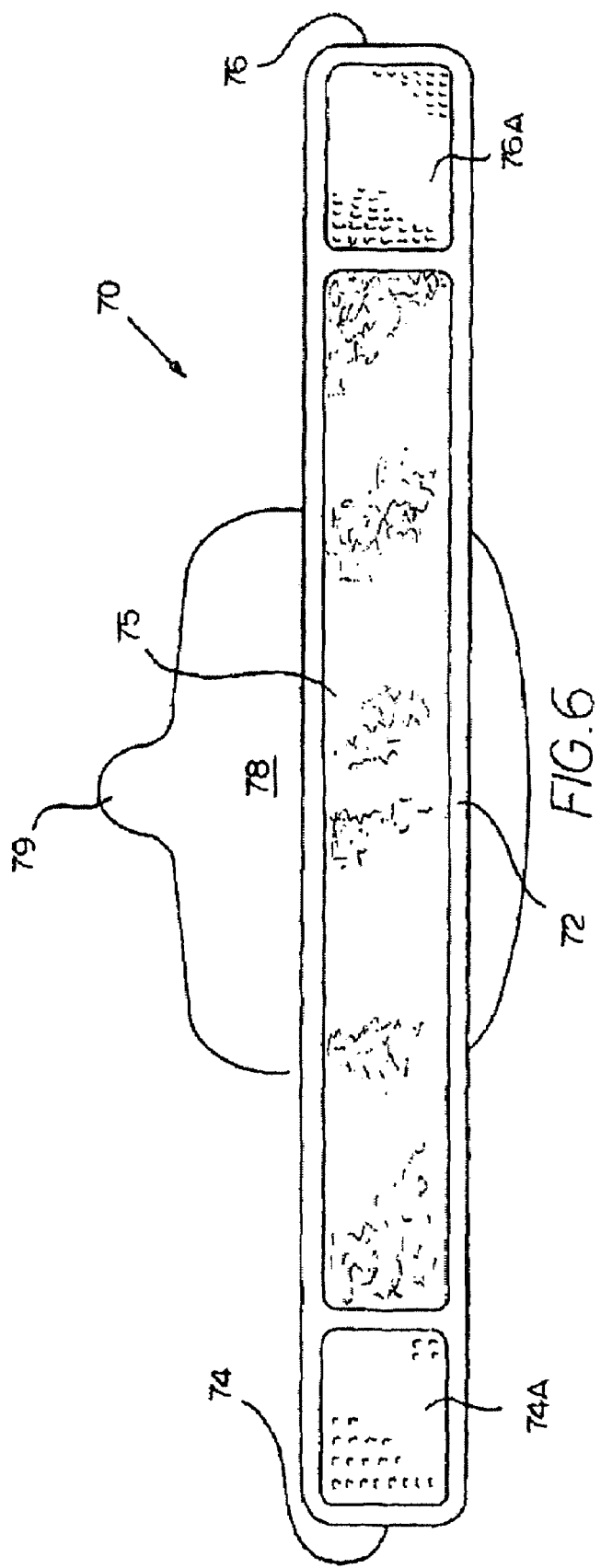
FIG. 6 is a front view of the lower adjustment strap of FIG. 1 in the open position, removed from the ankle brace.

The lower adjustment strap 70 is shown in more detail in FIG. 6 and includes a middle portion 72, a left end 74, and a right end 76. On the top surface of the lower adjustment strap 70 is hook and loop fastener material. In this embodiment, there are hook portions 74A, 76A near each end 74, 76, and a loop portion 75 extending between the hook portions-74A, 76A through the middle portion 72. There is also a cushion 78 secured to the rear surface of the middle portion 72 of the adjustment strap 70, and the middle portion of the cushion 78 defines an upwardly-extending tongue 79.

In use, the adjustment strap 70 functions in a very similar manner to a lace-up shoe. The left end 74 of the adjustment strap 70 is inserted through a slot 29 in the left upright portion 24 of the stirrup 20, and the right end 76 of the adjustment strap 70 is inserted through a slot 29 in the right upright portion 26 of the stirrup 20. The wearer puts on the ankle brace, pulls up on the tongue 79 and pulls both ends 74, 76 of the strap 70 toward the middle, where each of the hook portions 74A, 76A engages with the loop portion 75. This differs from a typical strap arrangement, in which one side of the strap is fixed to the brace, and there is only one free end of the strap, which is pulled in order to tighten the strap. Since this arrangement allows the wearer to pull on both ends of the strap 70 simultaneously in order to tighten the strap 70, the forces are applied more evenly and more like tightening the laces on a shoe. In fact, this arrangement could be used on other types of footwear that include a U-shaped stirrup, such as a shoe, in the same manner that it is used on this brace 10. The reason for the second set of slots 29 is to provide for additional adjustment, allowing the wearer to decide which set of slots is to be used.

Figure 6A:
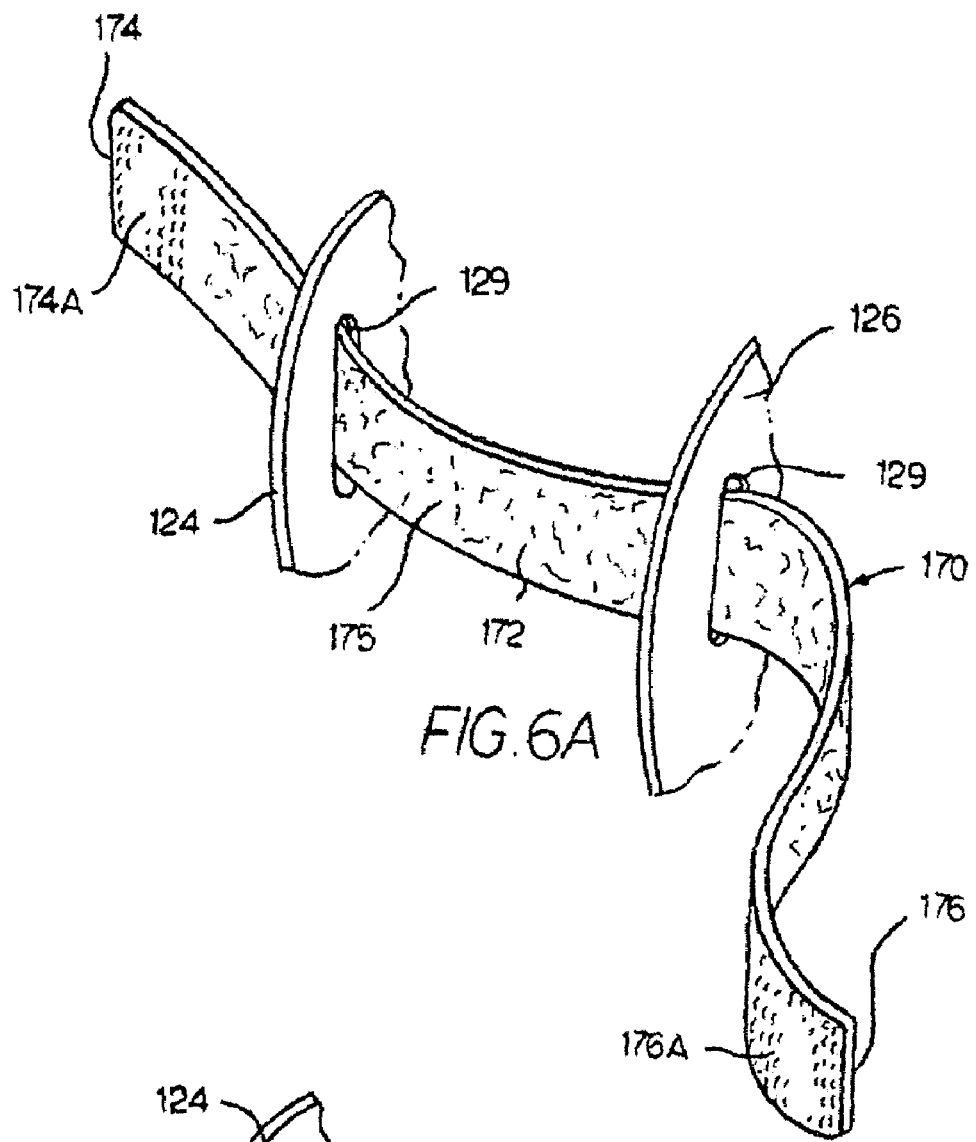
FIG. 6A is a view of another strap that may be used to tighten the ankle brace of FIG. 1.
Figure 6B:
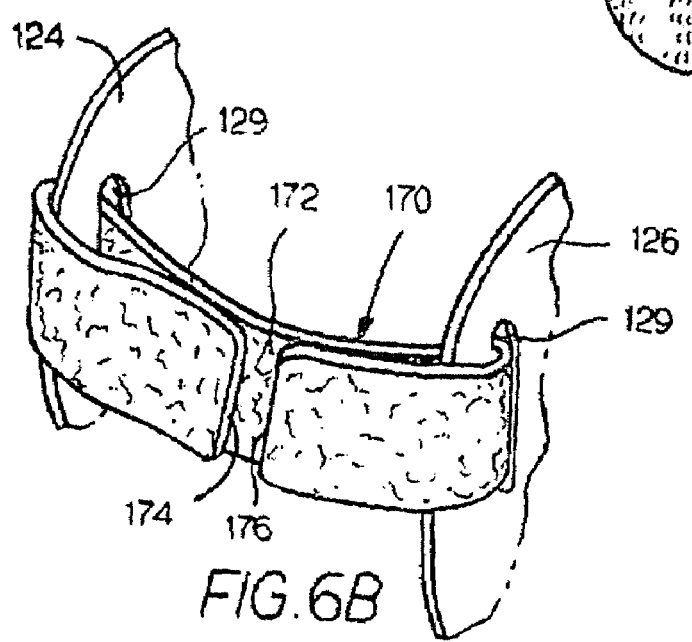
FIG. 6B is a view of the strap of FIG. 6A, showing one manner of tightening the strap.
Figure 6C:
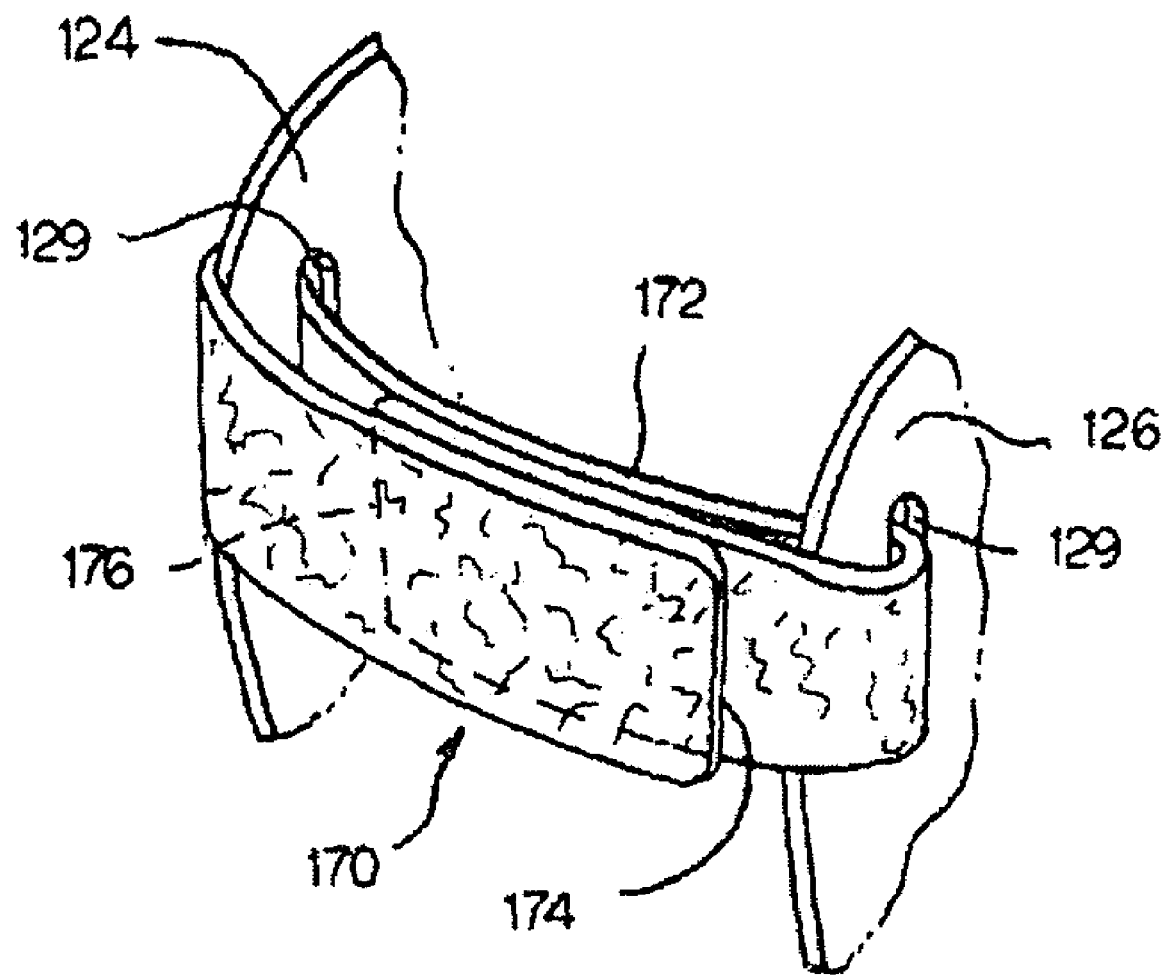
FIG. 6C is a view of the strap of FIG. 6A, showing a second manner of tightening the strap.

FIGS. 6A-6C show an alternate embodiment of an adjustment strap 170 that may be used with the ankle brace 10 (or with other articles of footwear). The article of footwear includes left and right upright side portions 124, 126, each defining at least one slot 129, as shown in FIGS. 6A-6C. Like the previous embodiment, the adjustment strap 170 includes a middle portion 172, a left end 174 and a right end 176, and on the top surface of the strap 170 there are hook portions 174A, 176A near each end 174, 176, and a first loop portion 175 extending through the middle portion 172 between the hook portions 174A, 176A. However, unlike the previous embodiment, there is no separate cushion in the central portion of the adjustment strap 170 and no tongue 79. In this embodiment, the entire back surface of the strap is covered by a second loop portion 177, which acts as a cushion and provides an additional surface to which one of the ends of the strap may be fastened, as will be explained in more detail later.

FIG. 6A is a view of the strap in its open position. The left end 174 of the strap 170 has been inserted through the slot 129 in the left portion 124, and the right end 176 of the strap 170 has been inserted through the slot 129 in the right portion 126. To tighten the brace around his foot, the wearer pulls the left and right ends 174, 176 of the strap simultaneously until there is a snug fit. Then, the wearer folds the left and right ends 174, 176 back over the middle portion 172 and fastens the left and right portions onto the strap 170 by means of the hook and loop fastener.

In FIG. 6B, the left and right ends 174, 176 are secured to the middle portion 172 by engaging each of the hook portions 174A, 176A (not visible in FIG. 6B) with the first loop portion 175 on the top surface of the strap 170. In FIG. 6C, the left and right ends 174, 176 overlap, with the right end 176 being secured to the middle portion 172 and the left end 174 being secured on top of the right end 176. Of course, the user could arrange the same strap 170 in reverse, with the left end being secured to the middle and then the right end being secured on top of the left end. In the arrangement shown in FIG. 6C, the hook portion 176A (not visible in FIG. 6C) near the right end 176 is engaged with the loop portion 175 on the top surface of the middle portion 172 of the strap 170, and the hook portion 174A (also not visible in FIG. 6C) near the left end 174 is engaged with the second loop portion 177 on the back of the right end 176 of the strap 170.

Figure 8:
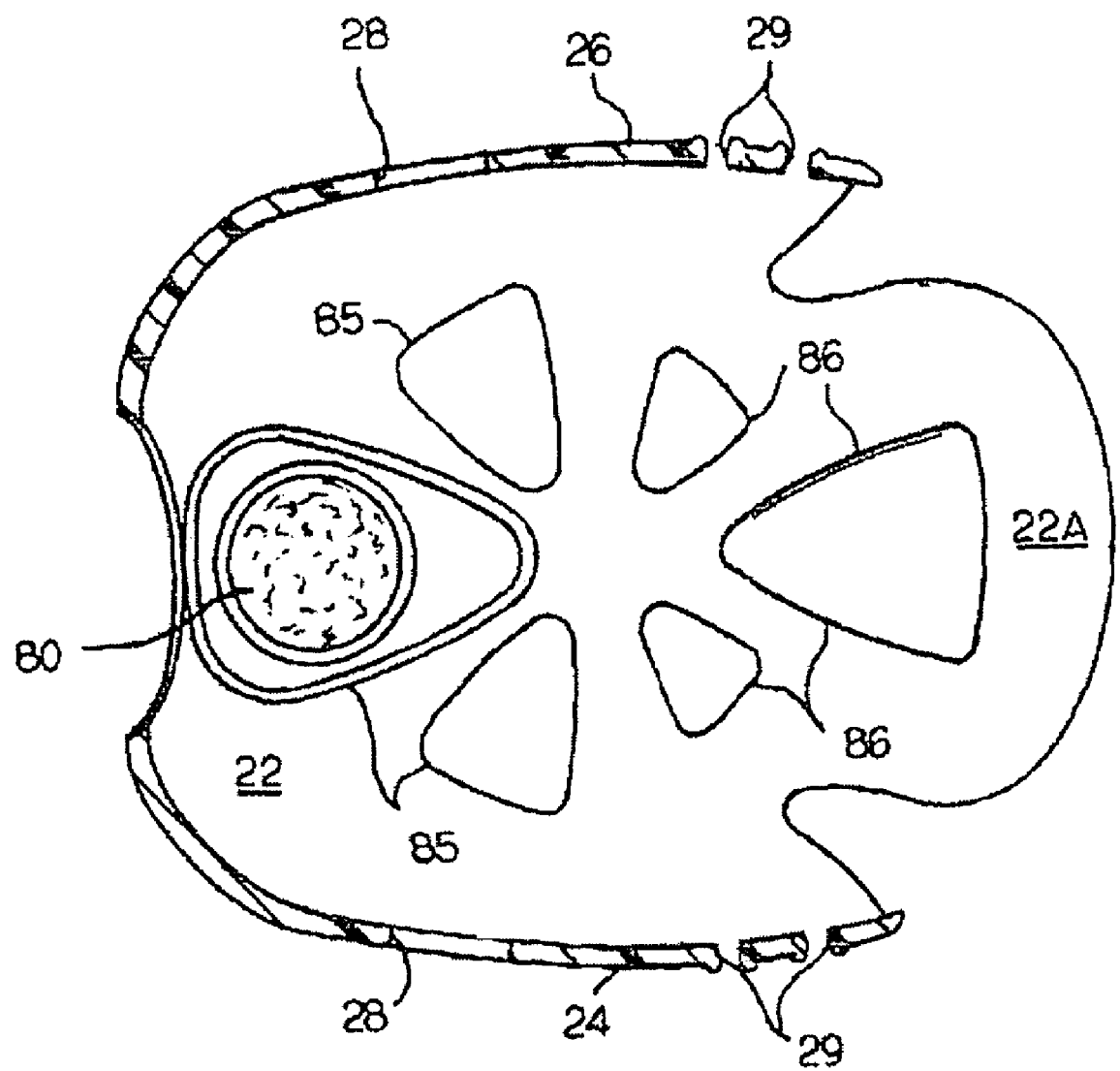
FIG. 8 is a view taken along line 8-8 of FIG. 2.

It should be noted that various forms of additional cushioning could be added between the ankle brace 10 and the wearer's ankle, such as one or more air cushions, a neoprene sleeve, or various other types of cushions, if desired. As shown in FIGS. 1, 3, and 8, some Velcro® dots 80 are adhered to the inner surface of this brace 10 in order to help secure such cushioning. Otherwise, the inner surface of the upper portion of the brace 10 preferably is smooth.

Figure 9:
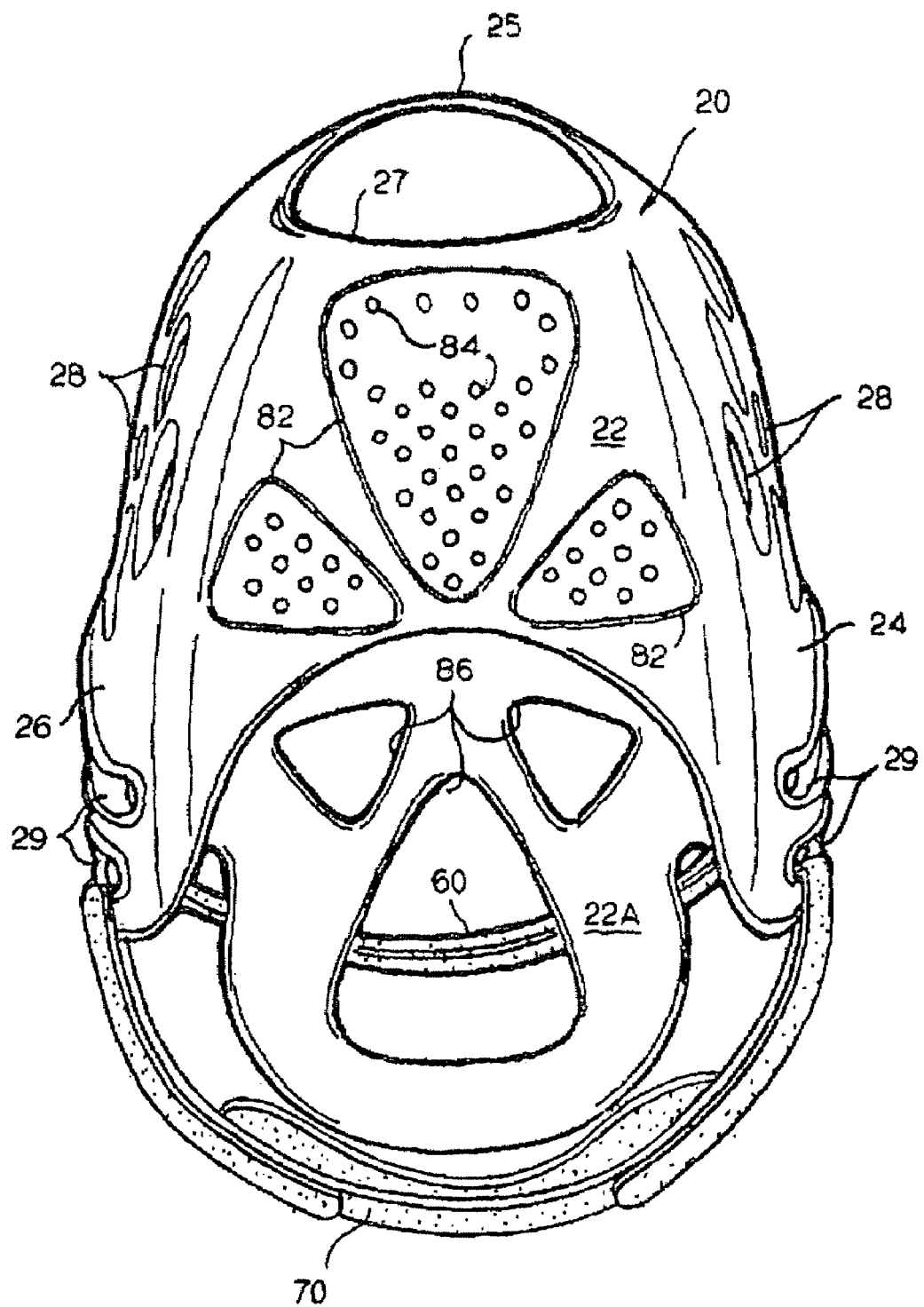
FIG. 9 is a bottom view of the brace of FIG. 1.

FIG. 9 is a view of the bottom of the ankle brace 10. The outside of the bottom portion 22 of the stirrup 20 has added texturing in order to provide some friction between the bottom portion 22 of the stirrup 20 and a shoe (or the ground, if a shoe is not being worn). The bottom portion 22 includes generally triangular shaped ridges 82 that protrude slightly downwardly from the bottom portion 22. These triangular shaped ridges 82 have thin, elongated sides, some of which extend mainly in the front-to-rear direction, and others of which extend mainly in the left-to-right direction. The ridges 82 extending in different directions form continuous shapes, which, in this case, are triangles. The elongated ridges help prevent the brace from sliding in a direction perpendicular to the direction of the ridge. Thus, the left-to-right-directed ridges help prevent the brace from sliding in a front-to-back direction, and the ridges that are directed in a more front-to-back direction help prevent the brace from sliding in a left-to-right direction. This makes the brace more stable so it functions better for the wearer.

Inside the ridges 82, there are circular recesses 84. The ridges 82 and recesses 84 provide an uneven bottom-surface for increased friction. As shown in FIG. 8, on the inside of the bottom portion 20, there are slight indentations 85 corresponding to the ridges 82 protruding on the outside of the bottom portion 20. FIGS. 8 and 9 also show that the forward projection 22A on the bottom portion 22 defines triangular openings 86. The forward projection 22A is substantially thinner than the rest of the bottom 20. It should be noted that other texture arrangements, besides the ridges 82 and recesses 84 shown in FIG. 9, may be used on the outside of the bottom portion 22 to provide friction, or the outside of the bottom portion 22 could be smooth.

Figure 10:
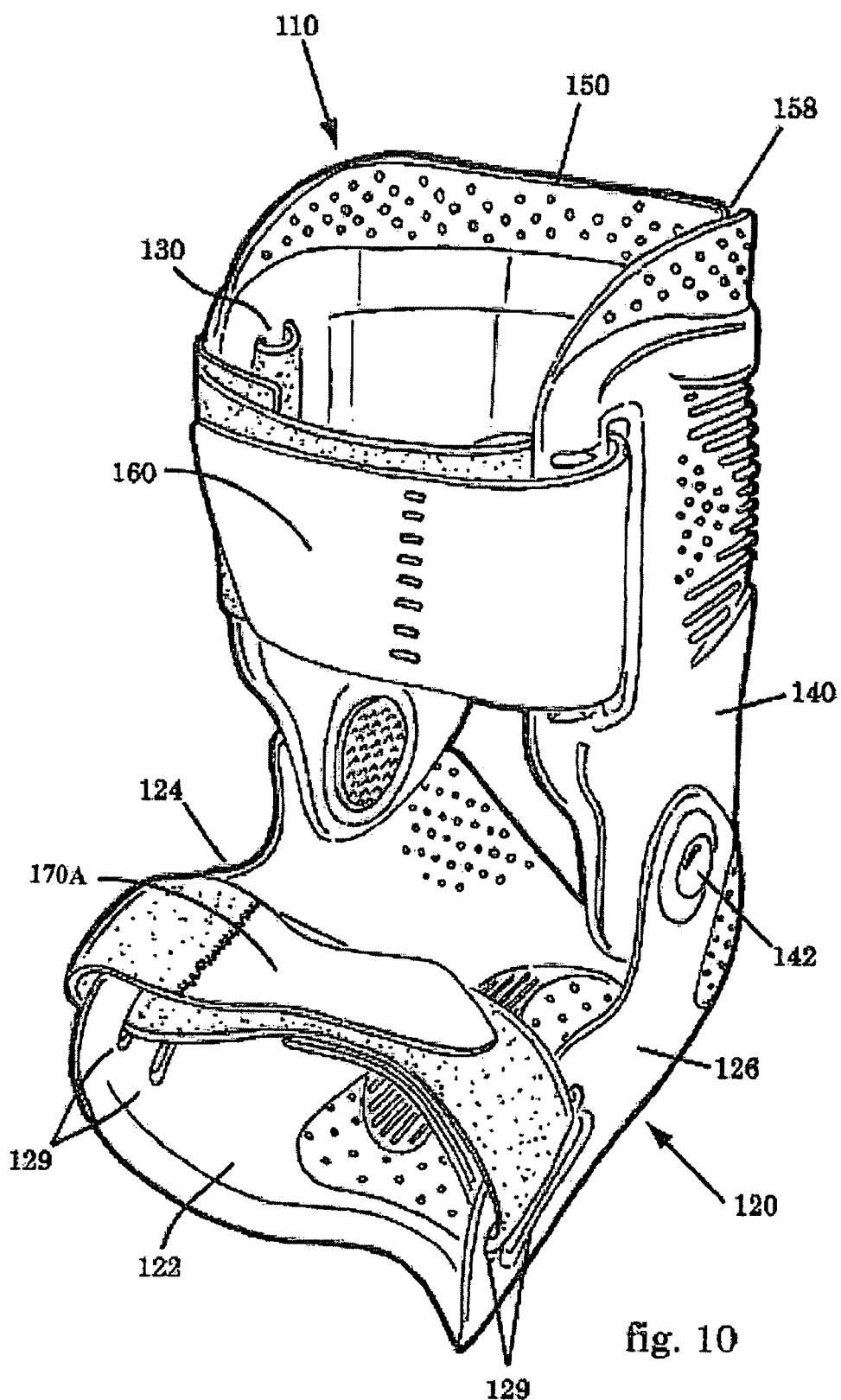
FIG. 10 is a front perspective view of a second embodiment of an ankle brace.

FIG. 10 is a second embodiment of a brace 110, which is very similar to the first embodiment 10. As with the previous embodiment, this embodiment is intended primarily to be worn inside a shoe, although it could be worn without a shoe, if desired. It includes a stirrup portion 120, left and right pivot legs 130, 140, and a rear cuff 150. The pivot legs 130, 140 pivot relative to the stirrup portion 120 about left and light pivot points 132, 142, respectively, each of which defines a pivot axis. As with the previous embodiment, the stirrup 120 includes a bottom portion 122 and left and right upright portions 124, 126. The bottom portion 122 extends beneath the wearer's foot, and the upright portions 124, 126 cradle the sides of the foot. As can be seen clearly in FIG. 11, in this embodiment, the upright portions 124, 126 extend a substantial distance forward of an imaginary vertical plane 132A extending through the pivot axis 132, and the parallel, arcuate, strap-receiving slots 129 extend in a generally horizontal direction, as compared with the strap-receiving slots 29 of the previous embodiment, which extend in a generally vertical direction.

Figure 11:
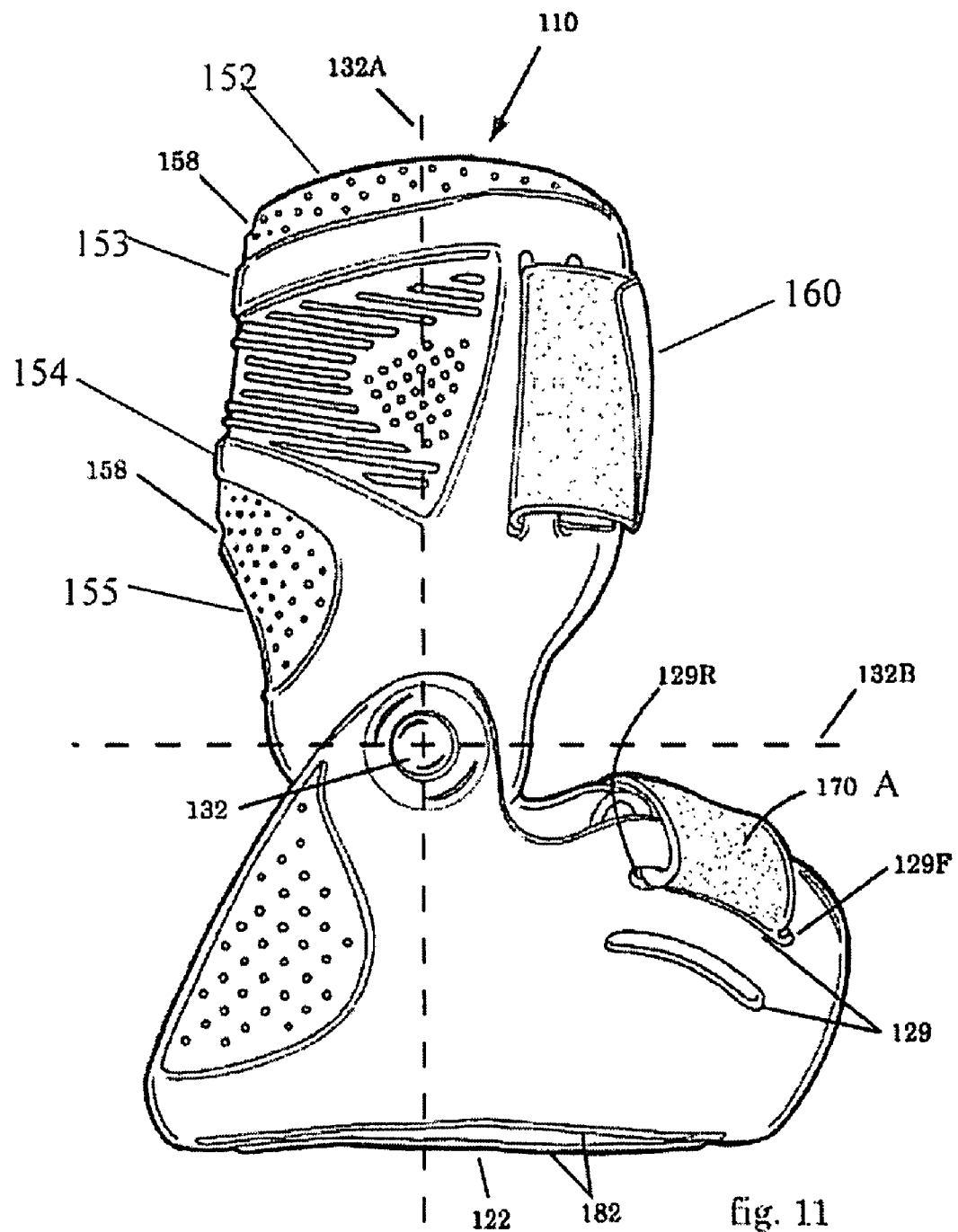
FIG. 11 is a left side view of the ankle brace of FIG. 10.

As shown in FIG. 11, the upper slot 129 is elongated and has a forward-most point or end 129F and a rearwardmost point or end 129R as well as a top side and a bottom side. The lower slot 129 is aligned side-to-side with the upper slot 129, so the upper side of the lower slot is adjacent to the lower side of the upper slot. The slots are essentially the same length, and the respective forward and rear ends of each pair of parallel slots also lie adjacent to each other, so the slots 29 are coextensive with each other for essentially their entire length. In this embodiment, the forward-most point 129F is 2.5 inches forward of the imaginary vertical plane 132A, and the rearwardmost point 129R is approximately 1⅛ inches rearward of the forward-most point 129F. It is preferable that the forward-most point 129F be at least 1.5 inches forward of the imaginary vertical plane 132A and more preferable that it be at least 2 inches forward of the imaginary vertical plane 132A. A strap 170A is received in the opposed upper strap-receiving slots 129 for tightening the stirrup 120 onto the wearer's foot. This embodiment differs from the previous embodiment, in that the strap 170A and slots 129 are located and oriented to pull the foot downwardly, against the bottom 122, whereas the lower strap 70 of the first embodiment pulled the foot rearwardly against the heel strip 25. It also means that this brace extends forward on the sides and bottom of the foot a substantial distance to provide good support. Since the brace 110 is essentially symmetrical about an imaginary vertical plane extending from front to back along the center of the brace, its left and right sides are almost identical, and the slots 129 on the left are directly opposite the slots 129 on the right.

The strap 170A can secure in any number of ways. As shown here, it uses a hook and loop type of fastener to secure both ends. Since the brace is symmetrical, the wearer is free to arrange the strap 170A to be pulled tight from either side, whichever is preferred, or to pull from both sides as described with respect to the previous embodiment. The arcuate shape of the slots 129 provides good surface area of contact between the strap 170A and the brace.

The uppermost point of the upper slot 129 is approximately ¾ inch below an imaginary horizontal plane 132B extending through the pivot axis 132. Since the pivot axis 132 aligns closely with the pivot point of the ankle joint, this means that the sides 124, 126 of the stirrup 120 wrap up a substantial distance around the sides of the foot for a substantial forward distance in order to give good support.

The upper strap 160 is secured in the same manner as in the first embodiment.

Figure 12:
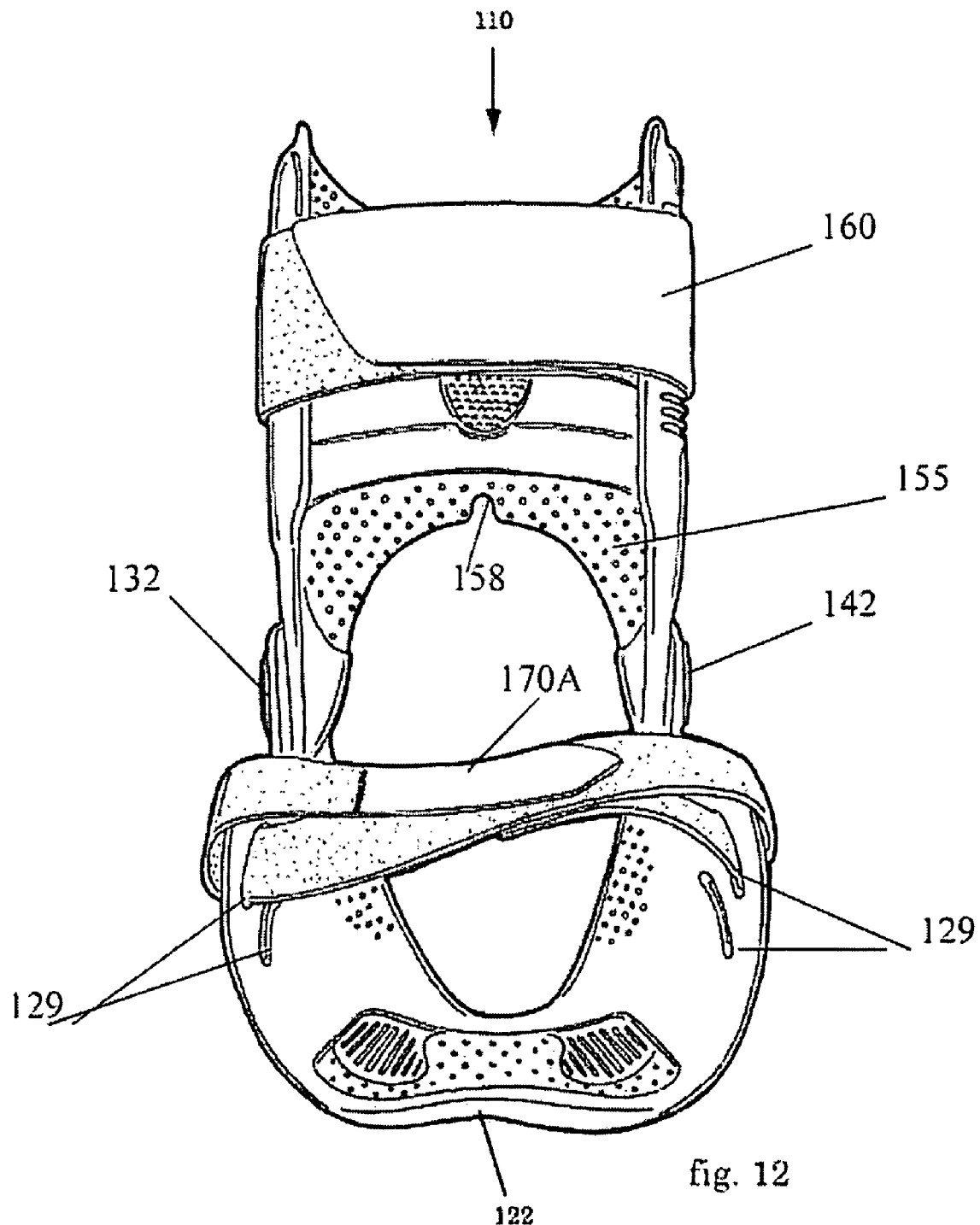
FIG. 12 is a front view of the ankle brace of FIG. 10.
Figure 13:
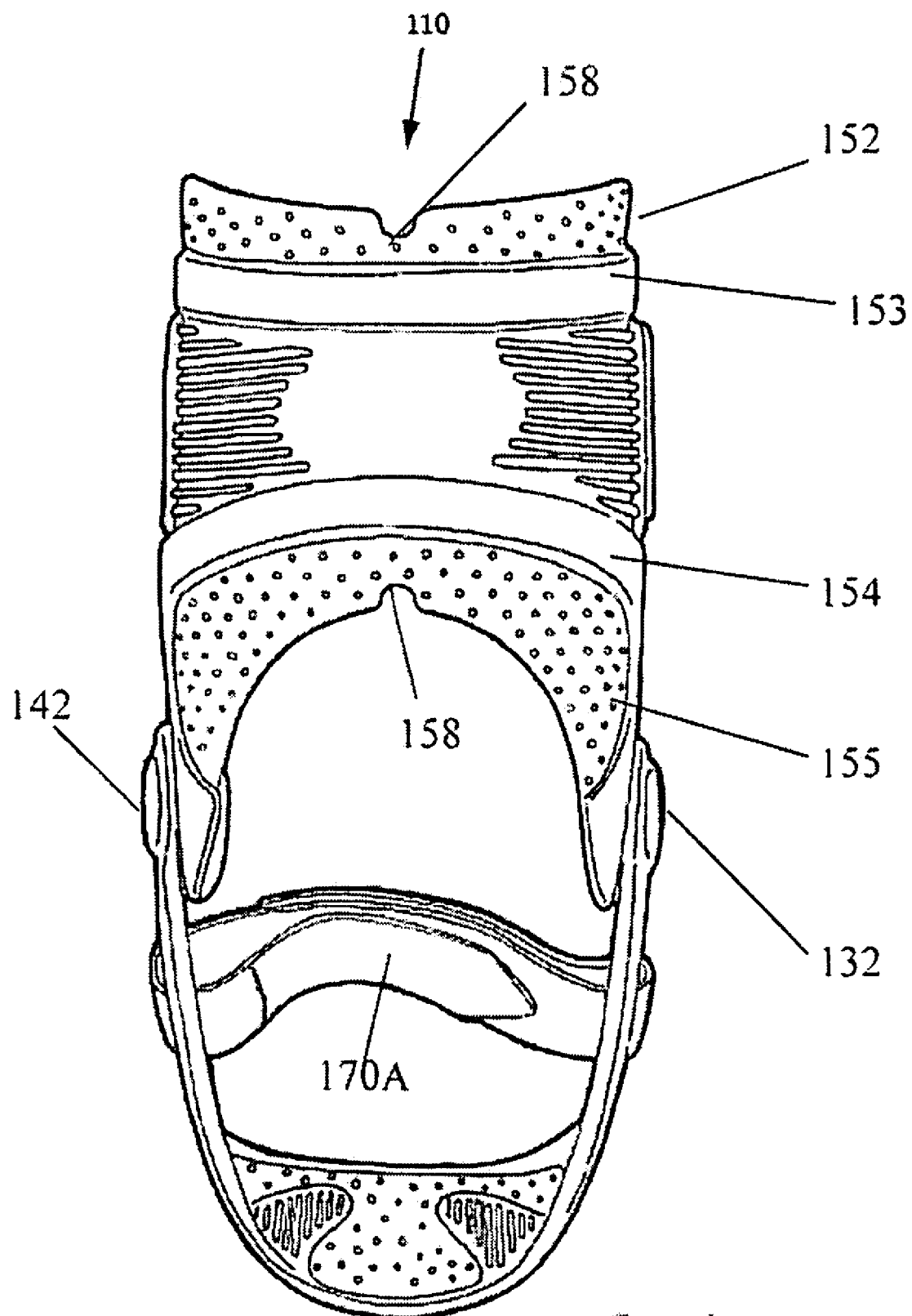
FIG. 13 is a rear view of the ankle brace of FIG. 10

FIG. 12 shows that there is texturing on the top surface of the bottom portion 122, which, in this embodiment, includes narrow, elongated ridges extending from front to back as well as recessed tiny dots. This helps prevent the wearer's foot from slipping relative to the brace 110 while not creating any discomfort for the wearer.

Figure 15:
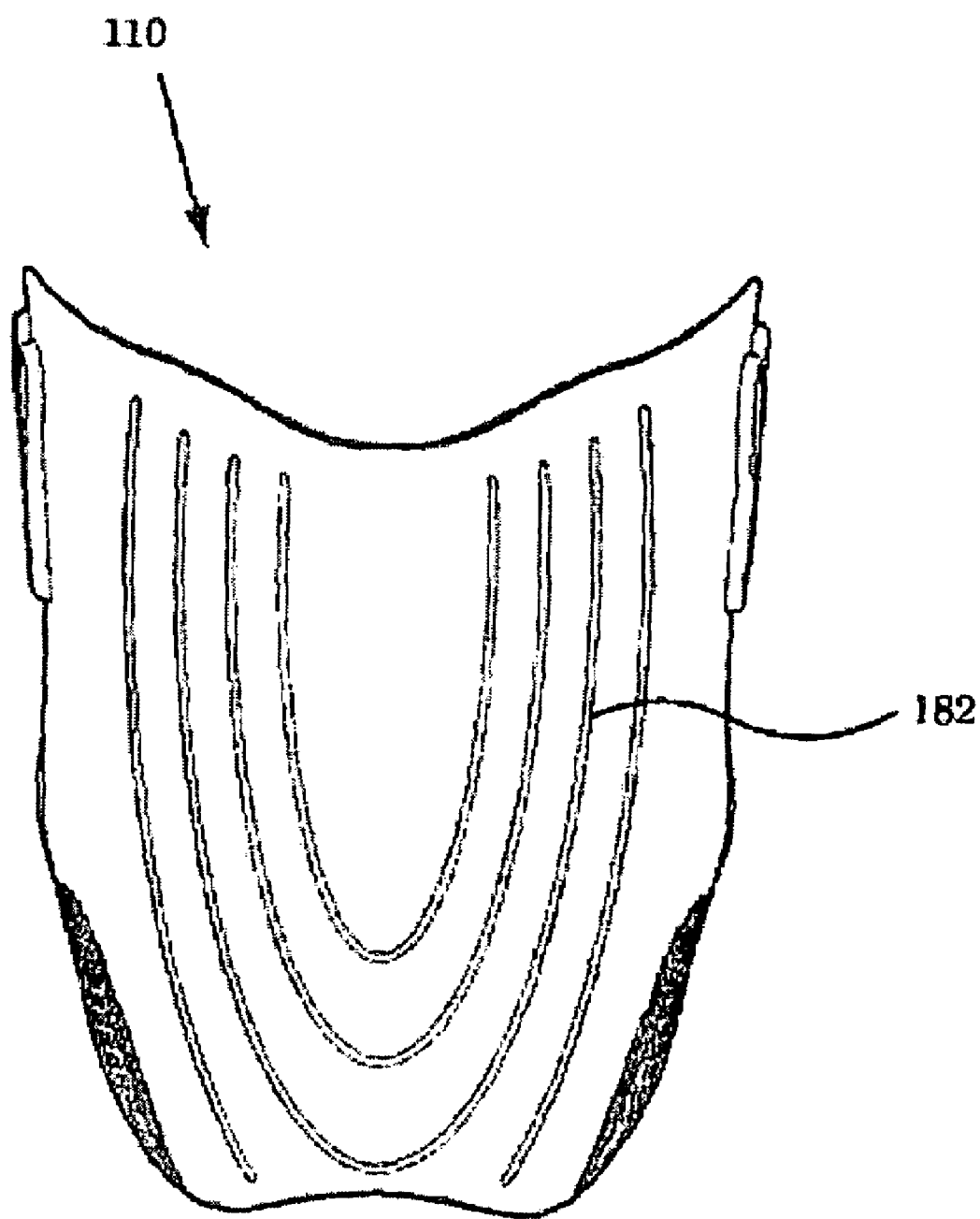
FIG. 15 is a bottom view of the ankle brace of FIG. 10.

On the bottom surface of the bottom portion 122, as shown in FIG. 15, are more aggressive thin, elongated ridges 182, which help prevent the brace 110 from slipping relative to the wearer's shoe. Since they concentrate the weight of the wearer over a very small surface area, they provide a large number of pounds per square inch of pressure with which to grip the shoe. These ridges project downwardly about 1⁄32 inches and have a width of about 1⁄32 inches. The width of the spaces between adjacent ridges 182 is much greater than the width of the ridges themselves, so the total surface area of the ridges is very small, which helps concentrate the weight of the wearer over a very small surface area. The ridges include portions that extend primarily in a front-to-rear direction and portions that extend primarily in a left-to-right direction. In this embodiment, pairs of front-to-rear ridge portions 182 are continuous with left-to-right portions, and the ridges 182 form a plurality of nested ellipsoids.

Figure 14:
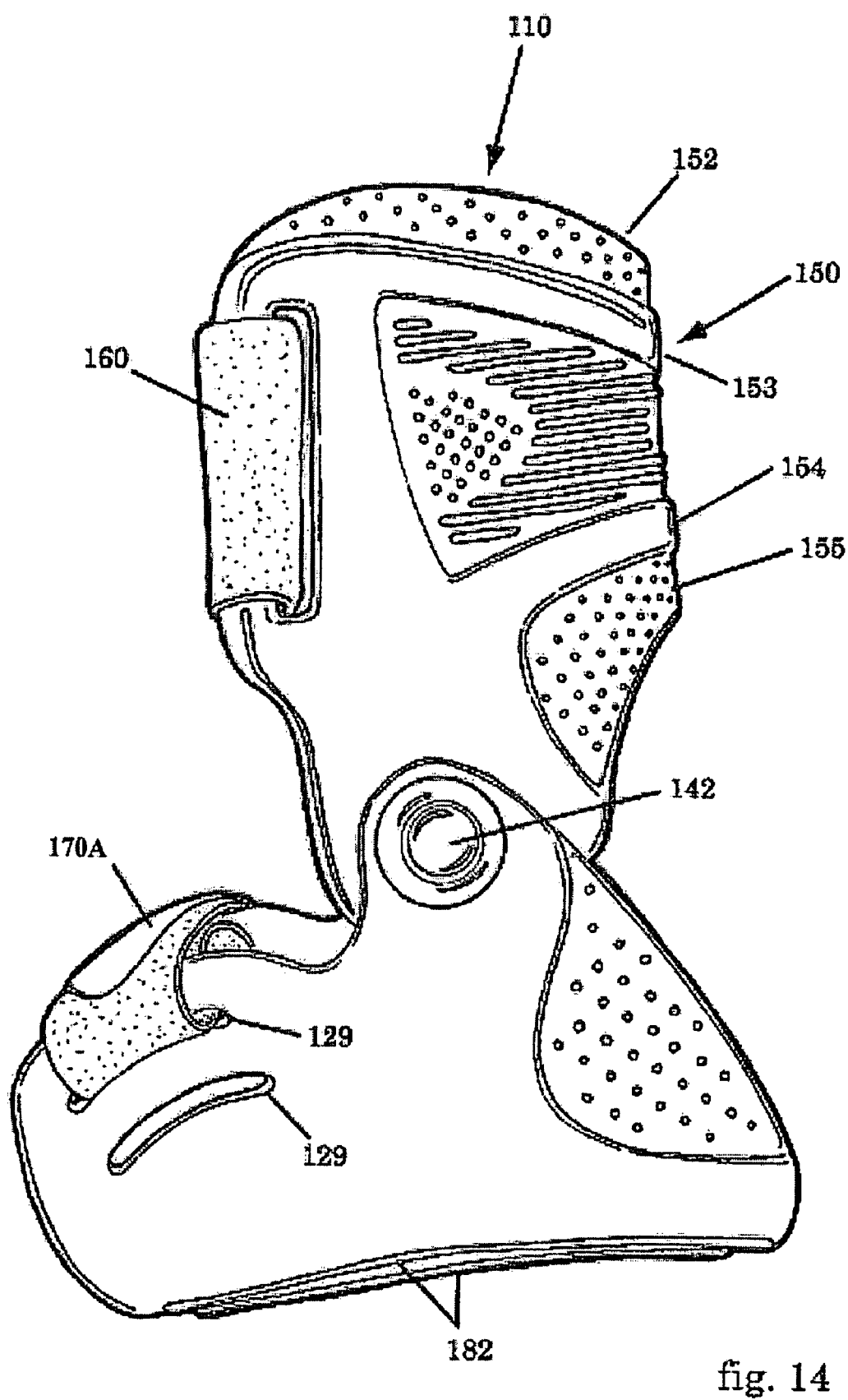
FIG. 14 is a right side view of the ankle brace of FIG. 10.

As shown best in FIG. 14, there are some portions of the brace 110 that are substantially thinner than others, making those portions more flexible, while the thicker portions are more rigid. For example, the rear cuff 150 has a plurality of bands extending from side to side. The upper and lower bands 152, 155, which form the top and bottom edges of the cuff 150, are thinner than some intermediate bands 153, 154, which allows the top and bottom edges of the cuff 150 to flex more, making the brace more comfortable for the wearer. Also, as in the previous embodiment, there are central indentations 158 in the top and bottom edges of the cuff 150, making the cuff 150 shorter at its center, so it can flex more easily in that shorter portion.

It will be obvious to those skilled in the foregoing description describes just one example of a product made in accordance with the present invention. It is understood that various modifications may be made without departing from the scope of the invention as claimed.

What is claimed is:

1. An ankle brace, comprising:
   a substantially U-shaped stirrup member, including a substantially flat bottom portion adapted to extend horizontally under a wearer's foot, and including left and right upright portions adapted to extend upwardly along the left and right sides of the wearer's foot; and
   left and right pivot leg members pivotably attached to said left and right upright portions at left and right pivot points, respectively, each of said pivot points defining a pivot axis;
   wherein each of said left and right upright portions defines a first strap-receiving slot extending forward of its respective pivot axis, with the first strap-receiving slot on the left upright portion lying opposite the first strap-receiving slot on the right upright portion, and each of said left and right upright portions also defines a second strap-receiving slot parallel to the respective first strap-receiving slot, each of said strap-receiving slots being elongated and having first and second ends, first and second sides, and a length, and the first and second slots on each upright portion being aligned side-to-side with each other so they are coextensive for at least a portion of their length.

2. An ankle brace as recited in claim 1, wherein the first and second strap-receiving slots on each upright portion are coextensive for most of their length.

3. An ankle brace as recited in claim 2, wherein said first and second strap-receiving slots on each of said left and right upright portions are substantially the same length.

4. An ankle brace as recited in claim 3, wherein each of said first strap-receiving slots is substantially horizontal and each of said second strap-receiving slots lies below its respective first strap-receiving slot.

5. An ankle brace as recited in claim 4, wherein both of said first strap-receiving slots and both of said second strap-receiving slots have an arcuate shape.

6. An ankle brace as recited in claim 5, wherein each of said first strap-receiving slots has a forward-most point at least 1½ inches forward of an imaginary vertical plane extending through its respective pivot axis.

7. An ankle brace as recited in claim 6, wherein said flat bottom portion of said stirrup member has a bottom surface defining a plurality of downwardly-projecting, thin, elongated, front-to-back directed ridges, with a plurality of spaces between the front-to-back directed ridges, wherein the width of the respective spaces is much greater than the width of the front-to-back directed ridges.

8. An ankle brace as recited in claim 1, wherein said first strap-receiving slot has an arcuate shape.

9. An ankle brace as recited in claim 1, wherein each of said first strap-receiving slots has a forward-most point at least 1½ inches forward of an imaginary vertical plane extending through its respective pivot axis.

10. An ankle brace as recited in claim 1, and further comprising a strap extending through both of said first strap-receiving slots.

* * * * *

UNITED STATES PATENT AND TRADEMARK OFFICE
CERTIFICATE OF CORRECTION

PATENT NO. : 7,615,026 B1 Page 1 of 1
APPLICATION NO. : 11/875448
DATED : November 10, 2009
INVENTOR(S) : Rick Peters et al.

It is certified that error appears in the above-identified patent and that said Letters Patent is hereby corrected as shown below:

Column 5, line 35, delete "light" and insert therefor --right--.

Signed and Sealed this

Fifth Day of January, 2010

David J. Kappos
*Director of the United States Patent and Trademark Office*